United States Patent [19]

Sempler

[11] 4,239,488
[45] Dec. 16, 1980

[54] ENCAPSULATED DENTURE ADHESIVE AND METHOD OF USE

[76] Inventor: Vance A. Sempler, R.D. #1, Box 101, Millport, N.Y. 14864

[21] Appl. No.: 48,998

[22] Filed: Jun. 15, 1979

[51] Int. Cl.³ .............................................. A61C 13/22
[52] U.S. Cl. ....................................., 433/180; 106/35
[58] Field of Search ............... 433/180, 183, 188, 168, 433/229; 106/35

[56] References Cited

U.S. PATENT DOCUMENTS

| | | | |
|---|---|---|---|
| 1,917,902 | 7/1933 | Rowe | 433/180 |
| 2,830,370 | 4/1958 | Rothrock | 106/35 |
| 2,889,625 | 6/1959 | Saffir | 433/180 |
| 3,029,188 | 4/1962 | Cyr et al. | 433/180 |
| 3,249,109 | 5/1966 | Maeth et al. | 433/180 |
| 3,284,901 | 11/1966 | Town | 433/188 |
| 3,575,915 | 4/1971 | Novak et al. | 433/180 |
| 3,990,149 | 11/1976 | Nedwig | 433/180 |

FOREIGN PATENT DOCUMENTS 117164  7/1943  Australia ................................ 433/180

*Primary Examiner*—Louis G. Mancene
*Assistant Examiner*—John J. Wilson

*Attorney, Agent, or Firm*—Clarence A. O'Brien; Harvey B. Jacobson

[57] ABSTRACT

An encapsulated adhesive is disclosed for use in fastening denture plates as well as a method for fastening denture plates by use of the encapsulated adhesive. A capsule which dissolves upon contact with the human skin contains a predetermined quantity of solid adhesive. When denture plates are to be fastened in the mouth of a wearer, a capsule containing the adhesive, preferably a capsule which has been softened in a moisturizing container, is placed between the denture plate and mouth after the plate has been loosely seated in its approximate final position in the oral cavity. When pressure is applied to the dental plate and the capsule is compressed, liquefaction of the capsule causes the adhesive to spread between the denture plate and supporting tissue of the wearer. After three capsules have been inserted at appropriate locations along the rim of contact of the denture plate with the mouth, and the capsule adhesive has become distributed along the contact area, the denture plate is securely seated in place. Upon loosening of a denture plate, the encapsulated adhesive of the present invention can be inserted to reseat the denture plate, thereby avoiding inconvenient customary manipulation of the denture plate.

8 Claims, 11 Drawing Figures

ENCAPSULATED DENTURE ADHESIVE AND METHOD OF USE

BACKGROUND OF THE INVENTION

Field of the Invention

The invention relates to a new form of denture adhesive for use in mounting denture plates in the oral cavity. The denture adhesive is provided in a capsule which undergoes liquefaction at or below the human body temperature. The invention also relates to a method for securing denture plates in the oral cavity of a wearer, and the invention further encompasses a softener kit or device for preparing encapsulated denture adhesives for use according to the method of the invention.

Disclosure Statement

Various gelatin adhesive preparations are known for pharmaceutical use such as are exemplified by U.S. Pat. No. 3,029,187, patented Apr. 10, 1962 with D. W. Steinhardt et al as the inventors, as well as U.S. Pat. No. 3,029,188, issued Apr. 10, 1962 to G. N. Cyr et al. Keumurdji in U.S. Pat. No. 3,921,293, issued Nov. 25, 1975, discloses an acrylic base dental prosthesis incorporating a mounting element for joining the base to a resilient molding which engages the gum of the wearer. Nedwig in U.S. Pat. No. 3,990,149, issued Nov. 9, 1976, discloses an adhesive foil for a dental prosthesis having a dry adhesive which swells under the action of moisture in the mouth. Other patents disclosing other concepts which could relate to the field of the invention include the following:

| | | |
|---|---|---|
| 3,249,109 | H. Maeth et al | May 3, 1966 |
| 3,284,901 | E. W. Town | Nov. 15, 1966 |
| 3,886,659 | M. F. Reifke | June 3, 1975 |

None of the above patents, however, discloses a method for fastening denture plates conveniently, easily, and without removing the plate from the mouth of the wearer, nor is there disclosed an article for facilitating such method of securing denture plates.

SUMMARY OF THE INVENTION

Drawbacks associated with prior art methods for securing denture plates by cumbersome conventional techniques are avoided with the present invention, where an adhesive is applied in an encapsulated form without the necessity to remove a denture plate from the mouth of the wearer. The encapsulated adhesive is insertable between the denture plate and the gum of the wearer, and the capsule containing the adhesive then undergoes liquefaction and spreads between the surface of the denture plate and the gum of the wearer.

Accordingly, an object of the invention is to provide a method for securing denture plates in the mouth of a wearer without the necessity of a step requiring removal of the plates and application thereto of a denture adhesive.

Another object of the invention is to provide an encapsulated denture adhesive which can be manually manipulated between a dental plate in the mouth of a wearer and the supporting gum of the wearer.

Still another object is to provide a softening kit comprising a moisturizing container for preparing the capsule for use according to the method of the invention.

Yet another object is to bond in place either a lower denture plate, an upper denture plate, or both an upper and lower plate sequentially, using the denture adhesive capsules of the present invention.

A further object is to provide a method for resetting a loose denture plate without removing the entire plate from the mouth of the wearer, even if only a portion of the loose plate requires fresh adhesive.

Another further object is to enable denture wearers to carry a supply of encapsulated denture adhesives on the person for convenient use whenever necessary.

Still another further object is to avoid wastage of denture adhesive by enabling no more than the necessary amount to be applied to dentures.

Yet another further object is to eliminate the inconvenience of soiling, spillage, and similar problems which often occur when using conventional denture creams or denture powders.

These, together with other objects and advantages which will become subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Many denture wearers utilize a denture adhesive cream found from experience to work well with the particular personal denture plates worn. Frequently, however, a problem arises when the wearer's denture plate becomes partially or completely loose, requiring the plate to be completely removed from the mouth, followed by a fresh application of denture adhesive cream. Moreover, in the majority of instances when a denture plate becomes loose, it is only partially loose and can be reset if adhesive can be applied to only that portion which has become separated. Accordingly, the inconvenience of mixing, applying, and performing the manipulative motions needed for resetting an entire denture plate can create special problems for the denture wearer during ordinary use of the denture plates, such as at work, while visiting, while traveling, shopping, or other similar situations away from home, and the like. A great many formulations of denture adhesive cream are presently marketed. Testing of many of the commercially available denture adhesive creams reveals that all those tested can be encapsulated successfully in a hollow capsule of the type conventionally used for pharmaceutical applications in which liquefaction occurs at or slightly below the human body temperature. Accordingly, many or all conventional adhesive creams can be so encapsulated, either in a manufacturing operation or by preparation of capsules filled with a particular preferred brand of denture adhesive by the consumer or wearer of denture plates. Prepared in encapsulated form, application of the adhesive is facilitated, inconvenience in applying a conventional adhesive cream is avoided, and saving of denture adhesive is achievable whenever a loosened denture plate can be reset by the simple expedient of inserting an adhesive capsule in the loosened area without removal of the denture plates and resetting of the entire plate in the mouth.

Figure 1:
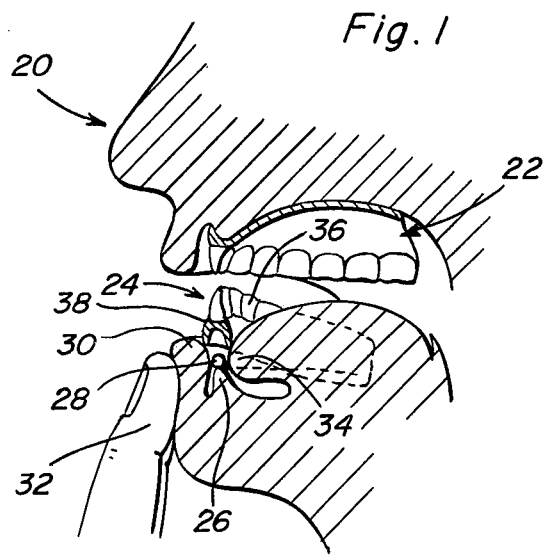
FIG. 1 is schematic side view of a denture wearer showing the first step in securing a lower denture plate in place, where a denture adhesive capsule has been placed centrally between the medial portion of the lower denture plate and gum portion of the mouth, the capsule being held in place by pressure from the denture wearer's finger acting on the lower lip and the wearer's tongue.
Figure 2:
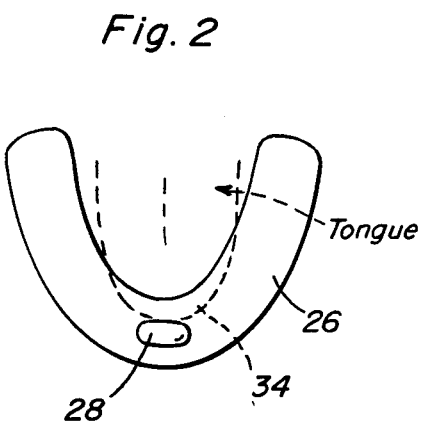
FIG. 2 is a schematized top view of the lower gum below a lower denture plate and associated capsule, showing in phantom the position of the tongue for retaining the capsule.
Figure 3:
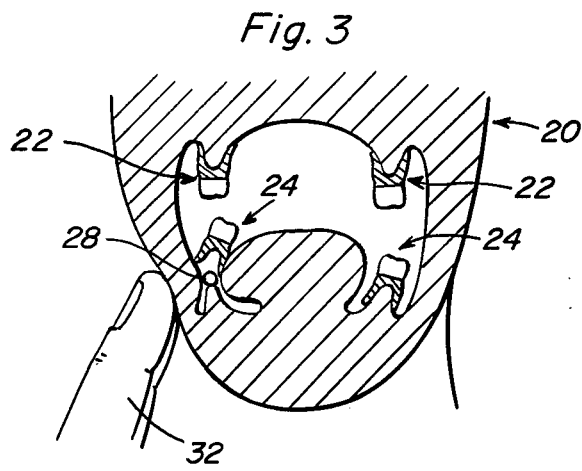
FIG. 3 is a front schematic view of the mouth of the denture wearer, showing the next step in seating the lower denture plate. A second capsule has been inserted between the right portion of the denture plate and the right part of the gum, and the capsule is held in place by pressure of the forefinger on the outside of the cheek and by the tongue.
Figure 4:
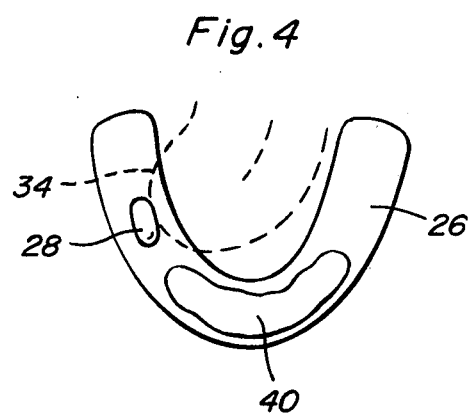
FIG. 4 is a schematized top view of the arrangement of FIG. 3, showing in phantom the position of the tongue against the second capsule, and showing further the liquefied and spread adhesive from the first capsule.
Figure 5:
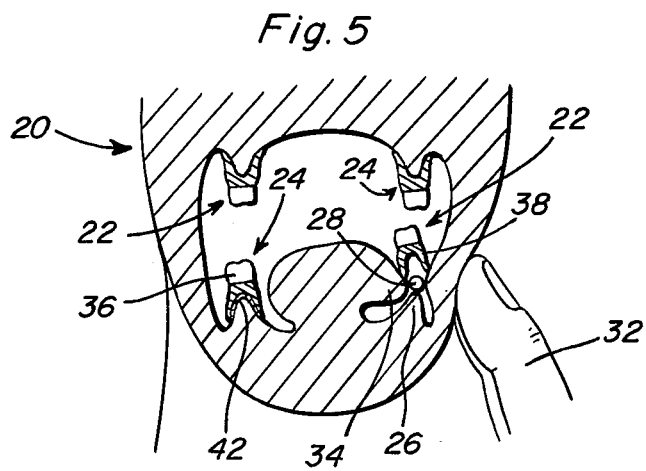
FIG. 5 is a front schematic view of the next step in applying the denture plate, showing a third capsule in the region between the left portion of the lower denture plate and the left gum.
Figure 6:
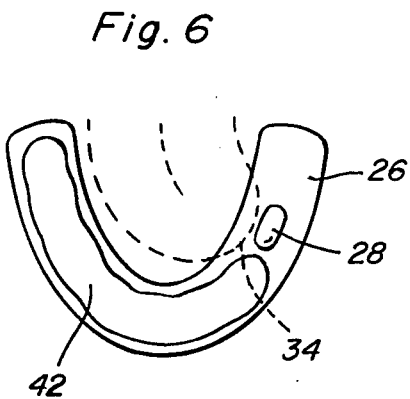
FIG. 6 is a schematized top view of the mouth illustrating the succeeding step in the method shown in FIG. 5, showing in phantom the position of the tongue in assisting to hold the third capsule in place, and further showing the adhesive from the first and second capsules after liquefaction and spreading over the lower denture plate.
Figure 7:
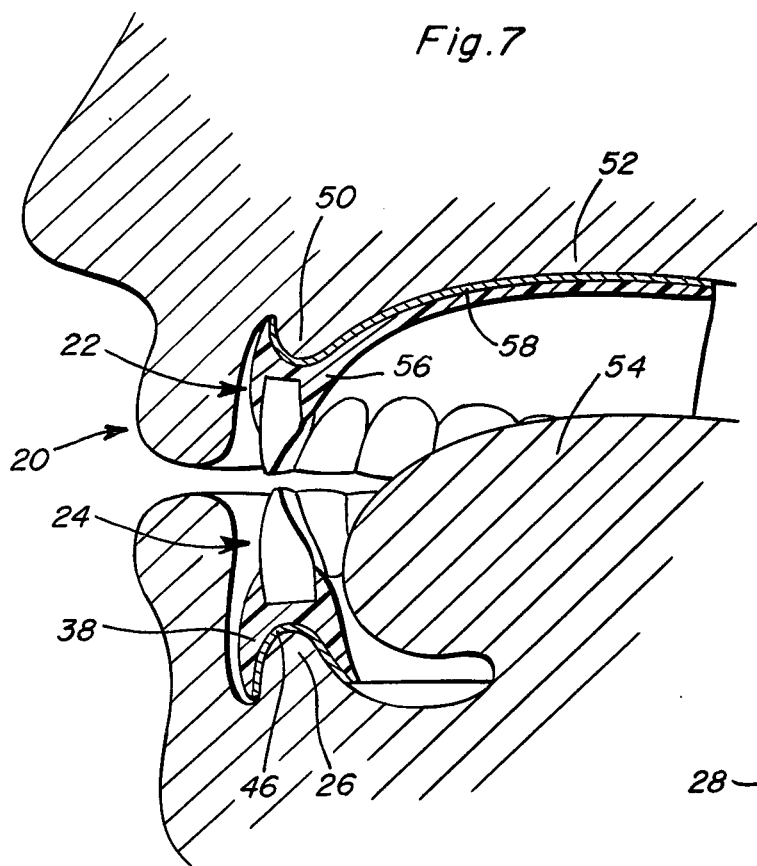
FIG. 7 is an enlarged schematized view of the mouth of a denture plate wearer after both upper and lower dentures have been affixed in place according to the method of the present invention.
Figure 9:
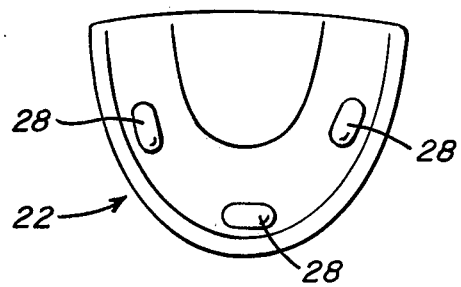
FIG. 9 is a top sectional view of an upper denture plate, showing the relative positioning of three capsules of the type shown in FIG. 8.

Referring now more specifically to FIG. 1, denture wearer 20 is furnished with upper denture plate 22 in place and is proceeding with the initial stage of the method of affixing lower denture plate 24 upon and along the entire oral cavity surface of gum 26 of wearer 20. Capsule 28 has been inserted between gum 26 and lower plate 24, and is held in place by pressure on lower lip 30 applied by forefinger 32, as well as counteracting pressure applied by the tip of tongue 34 of wearer 20. Denture plate 24 is constructed in a conventional manner and consists of artificial teeth 36 embedded firmly in base 38, which is preferably provided with an anatomic recess matching the shape of gum 26. Upon application of downward pressure on denture plate 24, capsule 28 undergoes liquefaction under the influence of temperature elevation as capsule 28 is pressed firmly against gum 26, the result of which is to cause the adhesive contained in capsule 28 to spread in the space between gum 26 and space 38, resulting in a layer of bonding adhesive such as that designated by the numeral 40 in FIG. 4. Next, the right portion of lower denture plate 24 is lifted and a second capsule 28 is inserted thereunder, as is best seen in FIG. 3. Again, capsule 28 is held in place by the tip of tongue 34 of wearer 20, as well as forefinger 32, giving the configuration shown in FIG. 4. Plate 24 is then forced downwardly, the capsule 28 then undergoing liquefaction and spreading into a layer of adhesive which merges with layer 40 to form layer 42 as best seen in FIG. 6. As a final step in the method of applying a denture plate using the encapsulated denture adhesive of the present invention, the left portion of lower denture plate 24 is elevated, as shown in FIG. 5, and a third capsule 28 is placed between base 38 and gum 26 of wearer 20. Again, capsule 28 is retained between forefinger 32 and the tip of tongue 34 of wearer 20. Downward compression of base 38 against gum 26 of wearer 20 causes capsule 28 to fuse and the adhesive to spread and join that of layer 42 in forming a continuous bonding layer 46 between base 38 of lower denture 24 and gum 26 of wearer 20. This layer is best seen in FIG. 7, showing lower denture plate 24 seated in place in the mouth of wearer 20. In addition, FIG. 7 illustrates in wearer 20 an upper denture plate 22 seated on upper gum 50 and palate 52 of wearer 20. In order to bond upper denture plate 22 in place, upper denture plate 22 is permitted to drop down in the mouth, and three denture adhesive capsules 28 are placed on upper plate 22 in the positions shown in FIG. 9. Plate 22 is then moved slowly upwardly by tongue 54, while simultaneously biting denture plates 24 and 22 together. Under compression against gum 50 by base 56 of upper denture plate 22, the three capsules 28 undergo liquefaction and spread to form a continuous bonding layer 58 to secure upper denture plate 22 to the roof of the mouth of wearer 20.

Figure 10:
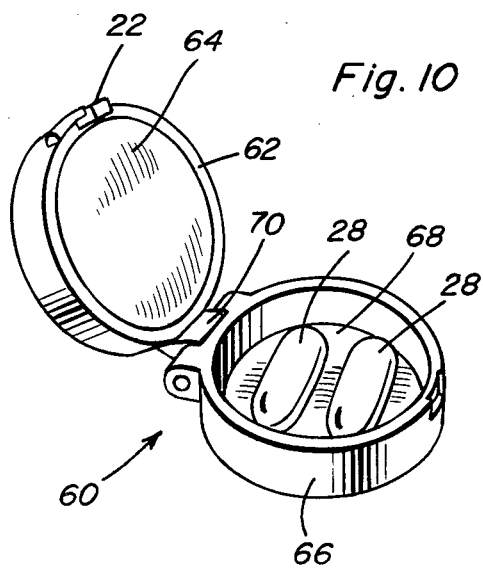
FIG. 10 is a perspective view of a softener kit for convenient carrying and softening of encapsulated denture adhesive, two capsules of the type shown in FIG. 8 being present in the softener kit.
Figure 11:
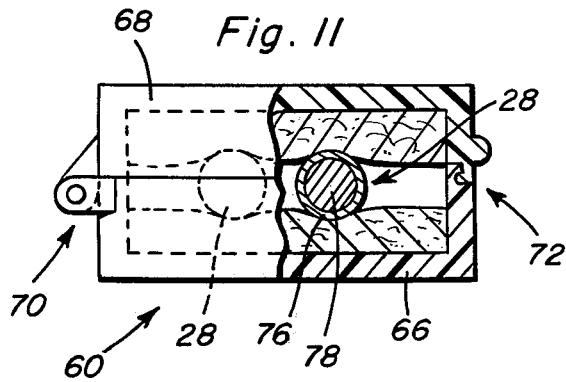
FIG. 11 is a side view, partly in section, of the softener kit of FIG. 10, showing moistenable wicking material, such as cotton, between which layers the capsules are held in softened configuration ready for use.

In all instances of bonding lower denture plates as well as upper denture plates, it is advantageous to first soften the denture adhesive capsule 28 in order to cause the denture plate to settle in place more quickly. This can be accomplished either by working saliva in the mouth over and around the plate which compresses a capsule against a surface of the mouth or can be achieved by means of a softener kit for holding capsules in a box-like enclosure provided with a moist wicking material, such as cotton which surroundingly moisturizes the capsules. For instance, FIG. 10 shows container box 60, container box 60, comprising top portion 62, which contains a thickness 64 of moist cotton, and bottom portion 66, which also contains a thickness 68 of moist cotton. Hinge means 70 joins the upper and lower portions pivotally, and latch means 72 permit a manually detachable snap fit to engage the upper and lower portions of box 60 to contain capsules 28 therein.

Figure 8:
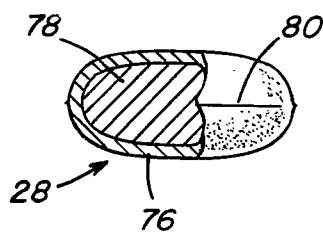
FIG. 8 is a side view, partly in section, of an encapsulated denture adhesive, the capsule shown in FIG. 8 being one of a plurality of sizes selected for a particular application.

Capsule 28 is seen in FIG. 8 to comprise outer shell 76 and adhesive 78 contained therein. Shell 76 is made from a material and in a manner well known in the art of pharmacy so as to liquefy upon contact with human skin. Although capsule 28 in FIG. 8 is seen to have seam 80, indicating machine manufacture, other alternative constructions can also be used to provide a hermetic seal, including two interfitting hollow oval portions adaptable for use by wearer 20, whereby the user can prepare individual capsules from a supply of interfitting capsule shells and a brand of denture adhesive cream or other adhesive preparation which has been found most suitable in the experience of the wearer.

When applied in capsule form, considerable wastage is avoided, and convenience to the user is promoted, as pointed out hereinabove. Furthermore, when the method of the present invention is followed, it has been found that only about two minutes is required normally to replace all three capsules on one plate. If only one denture capsule must be replaced, due to a loosened portion of a denture plate, for example, it has been found to ordinarily require just over one-half minute to replace the one denture adhesive capsule. It is apparent that considerable savings of time are represented by these results, by contrast with the period of several minutes required by conventional methods of denture replacement involving removal of the denture plates, preparation and application of new denture adhesive, and replacement of the plates in the mouth. Moreover, with the softener kit of the present invention, it is possible to utilize capsules which will undergo liquefaction in about 10–15 seconds, thereby offering the possibility of shortening even further the time needed to replace the capsules. Accordingly, the encapsulated denture adhesive of the present invention represents a new and unique way to contain a denture adhesive, with the result that it is feasible and simple for a denture wearer to bond loose denture plates back in place without removing the plates from the mouth.

The denture adhesive capsules of the present invention can be made in a variety of lengths and diameters in order to fit all reasonable variations of denture plate size, and to contain precisely the correct amount of denture adhesive to securely bond the denture plates firmly in place.

With use of the softener kit of the present invention, an ample supply of denture adhesive capsules can be carried conveniently in a wearer's pocket or purse for immediate use without the inconvenience of requiring extensive manipulation, as well as a location of privacy which frequently causes disruption of personal routine of the denture plate wearer.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A denture adhesive capsule for bonding a denture plate in the oral cavity of a wearer comprising a capsule shell and a denture adhesive contained hermetically within the shell, the adhesive being releasable from the capsule when the capsule is inserted in the oral cavity of the wearer and compressed thereon by the denture plate, the capsule shell being a composition which undergoes liquefaction at a temperature at or slightly below normal human body temperature, whereby said compression causes the adhesive to form a bonding layer between the denture plate and the oral cavity.

2. The capsule of claim 1 wherein said capsule shell is softenable under moisturization at ambient temperature, whereby the speed of said liquifaction and bonding is accelerated.

3. A method for bonding a loose denture plate in place on the gums of the oral cavity of a wearer, the plate comprising a plurality of artificial teeth embedded in a base having an anatomic recessed portion matching the gum shape, the loosened denture plate having a loosened base portion, the bonding taking place with a denture adhesive contained in a capsule hermetically containing the adhesive in a capsule shell which is capable of undergoing liquefaction at a temperature at or slightly below human body temperature, the method comprising the following steps:
   (a) separating the loosened denture plate from the gum;
   (b) inserting the denture adhesive capsule between the gum and the separated portion of the base of the plate;
   (c) holding the capsule in place and compressing the plate in the direction of the gum to apply pressure on the capsule; and
   (d) maintaining said pressure until the capsule melts and the adhesive spreads to form a bonding layer between the base and gum.

4. A method for bonding a lower denture plate in place on the gums of the oral cavity of a wearer, the lower plate comprising a plurality of artificial teeth embedded in a base having an anatomic recessed portion matching the gum shape, the bonding taking place with a denture adhesive contained in three capsules hermetically containing the adhesive in a capsule shell which is capable of undergoing liquefaction at a temperature at or slightly below human body temperature, the method comprising:
   (a) placing the lower denture plate in the oral cavity in conforming relation to the gum;
   (b) inserting a first denture adhesive capsule between the base of the plate and the gum near the medial position of the plate and the medial position of the gum;
   (c) holding the first capsule in place and compressing the plate downwardly to apply pressure on the capsule;
   (d) maintaining said pressure until the capsule melts and the adhesive spreads to form a bonding layer between the base and the gum;
   (e) raising a side of the lower plate upwardly to give an uplifted base portion;
   (f) inserting a second capsule between the uplifted base portion and the gum;
   (g) holding the second capsule in place and compressing the plate downwardly to apply pressure on the second capsule;
   (h) maintaining said pressure until the capsule melts and the adhesive spreads between the base and the gums;
   (i) raising the opposite side of the plate upwardly to give an uplifted base;
   (j) inserting a third capsule between the uplifted base portion and the gum;
   (k) holding the third capsule in place and compressing the plate downwardly to apply pressure on the second capsule; and
   (l) maintaining said pressure until the third capsule melts and the adhesive spreads to form a bonding layer between the base and the gum.

5. The method of claim 4 wherein the capsule in step (c), step (g) and step (k) is held in place by outwardly directed pressure from the tip of the tongue of the wearer and opposing inwardly directed pressure from a digit of the wearer acting through the face of the wearer.

6. The method of claim 5 wherein the following additional step is carried out on the three capsules before inserting in step (b), step (f) and step (j): softening by moisturizing the capsules.

7. A method for bonding an upper denture plate in place on the upper gums in the oral cavity of a wearer, the plate comprising a plurality of artificial teeth embedded in a base having an anatomic recessed portion matching the gum shape, the bonding taking place with a denture adhesive contained in three capsules hermetically containing the adhesive in a capsule shell which is capable of undergoing liquefaction at a temperature at a slightly below human body temperature, the method comprising:

(a) placing the upper denture plate in the oral cavity in conforming relation to the gums,
(b) inserting the three denture adhesive capsules on the recessed portion of the upper denture plate in an approximately medial position and substantially equidistant sidewise positions;
(c) compressing the plate upwardly to apply pressure on the three capsules; and
(d) maintaining said pressure until the capsules melt and the adhesive spreads to form a bonding layer between the base and the gum.

8. The method of claim 7 wherein the capsules are softened by moisturizing before inserting between the base and the upper plate in step (b).

* * * * *